(12) United States Patent
Marcoe

(10) Patent No.: US 9,433,740 B2
(45) Date of Patent: Sep. 6, 2016

(54) APPARATUS FOR SECURING A TRACHEAL TUBE OR THE LIKE TO A PATIENT

(71) Applicant: Gregory P. Marcoe, Midland, MI (US)

(72) Inventor: Gregory P. Marcoe, Midland, MI (US)

(73) Assignee: Majorus Medical, Inc., Decatur, IL (US)

( * ) Notice: Subject to any disclaimer, the term of this patent is extended or adjusted under 35 U.S.C. 154(b) by 217 days.

(21) Appl. No.: 14/451,996

(22) Filed: Aug. 5, 2014

(65) Prior Publication Data

US 2014/0338674 A1 Nov. 20, 2014

Related U.S. Application Data

(62) Division of application No. 13/028,895, filed on Feb. 16, 2011, now Pat. No. 8,794,240.

(60) Provisional application No. 61/338,205, filed on Feb. 16, 2010.

(51) Int. Cl.
*A61M 16/04* (2006.01)
*A61M 25/02* (2006.01)

(52) U.S. Cl.
CPC ..... *A61M 16/0497* (2013.01); *A61M 16/0447* (2014.02); *A61M 25/02* (2013.01); *A61M 2025/0266* (2013.01); *A61M 2209/06* (2013.01)

(58) Field of Classification Search
CPC .............. A61M 16/0497; A61M 16/0447; A61M 25/02; A61M 2209/06; A61M 2025/0266

USPC ............ 128/207.17, 200.26, 207.14, 207.15; 604/180, 540–544

See application file for complete search history.

(56) References Cited

U.S. PATENT DOCUMENTS

| | | | |
|---|---|---|---|
| 3,430,300 A | 3/1969 | Doan | 24/304 |
| 3,834,380 A | 9/1974 | Boyd | 604/180 |
| 3,927,676 A * | 12/1975 | Schultz | A61M 25/02 128/207.17 |
| 4,275,721 A | 6/1981 | Olson | 604/180 |
| 4,460,356 A * | 7/1984 | Moseley | A61M 25/02 604/180 |
| 4,598,004 A | 7/1986 | Heinecke | 428/41.5 |
| 4,838,868 A | 6/1989 | Forgar et al. | 604/180 |
| 4,867,146 A | 9/1989 | Krupnick et al. | 128/858 |
| 5,038,778 A | 8/1991 | Lott | 128/207.17 |
| 5,042,466 A | 8/1991 | McKnight | 602/52 |
| 5,219,336 A | 6/1993 | Wilk | 604/180 |
| 5,306,233 A | 4/1994 | Glover | 602/41 |
| 5,448,985 A * | 9/1995 | Byrd | A61M 16/0488 128/207.17 |
| 5,507,285 A | 4/1996 | Mota | 128/207.17 |
| 5,546,938 A | 8/1996 | McKenzie | 128/207.17 |
| 5,556,375 A | 9/1996 | Ewall | 602/58 |
| 5,638,814 A | 6/1997 | Byrd | 128/207.17 |
| 7,524,307 B2 | 4/2009 | Davis et al. | 604/180 |
| 7,544,186 B2 | 6/2009 | Davis et al. | 604/180 |
| 2008/0173310 A1 | 7/2008 | Marcoe | 128/207.7 |
| 2009/0240207 A1 | 9/2009 | Davis et al. | 604/180 |
| 2011/0015557 A1 | 1/2011 | Aali et al. | 602/56 |

* cited by examiner

*Primary Examiner* — Tan-Uyen (Jackie) T Ho
*Assistant Examiner* — Mark Wardas
(74) *Attorney, Agent, or Firm* — Alvin T. Rockhill

(57) ABSTRACT

An improved method for securing a tracheal tube, an adjunct tube, and oropharyngeal tube, a nasogastric tube, a laryngeal tube or laryngeal mask airway to a patient utilizing an elongated strip of adhesive tape, which is specifically adapted therefor.

8 Claims, 5 Drawing Sheets

APPARATUS FOR SECURING A TRACHEAL TUBE OR THE LIKE TO A PATIENT

This is a divisional of U.S. patent application Ser. No. 13/028,895, filed on Feb. 16, 2011, which claims the benefit of U.S. Provisional Patent Application Ser. No. 61/338,205, filed on Feb. 16, 2010. The teachings of U.S. Patent Application Ser. No. 61/338,205 and U.S. patent application Ser. No. 13/028,895 are incorporated herein by reference in their entirety.

BACKGROUND OF THE INVENTION

The instant invention relates to apparatus comprising adhesive tape for securing a tracheal tube or the like to a patient. Various apparatus comprising adhesive tape are available for securing a tracheal tube or the like (such as an airway adjunct tube, an oropharyngeal tube, a nasogastric tube, a laryngeal tube or laryngeal mask airway) to a patient. For example, U.S. Pat. No. 3,927,676 discloses tape having a central non-adhesive portion extending around the back of the neck of the patient, the tape having bifurcated adhesive coated ends for wrapping around a tracheal tube and then attachment back to the tape to secure the tracheal tube to the patient. U.S. Pat. Nos. 5,038,778 and 5,306,233 disclose tape having a central non-adhesive portion extending around the back of the neck of the patient, the tape having bifurcated adhesive coated ends for wrapping around a tracheal tube and attachment to the patient to secure the tracheal tube to the patient. U.S. Pat. No. 5,546,938 discloses tape having a central non-adhesive portion extending around the back of the neck of the patient, the tape having bifurcated adhesive coated ends for wrapping around a tracheal tube and attachment to the upper lip to secure the tracheal tube to the patient. U.S. Pat. No. 5,638,814 discloses tape attached to central non-adhesive strap extending around the back of the neck of the patient, the tape having a central adhesive coated X-shaped portion for wrapping around a tracheal tube to secure the tracheal tube to the patient.

Despite the advances made in the art of apparatus and methods for securing a tracheal tube or the like to a patient, such apparatus and methods have not supplanted the use of un-sterilized rolls of adhesive tape even though the use of such tape may provide a means for cross-contamination and infection. Therefore, there remains a need for apparatus and methods for securing a tracheal tube or the like to a patient that are easily used and which reduce the possibility for cross-contamination and infection.

SUMMARY OF THE INVENTION

The instant invention provides an apparatus and method for securing a tracheal tube, an adjunct tube, an oropharyngeal tube, a nasogastric tube, a laryngeal tube or laryngeal mask airway to a patient. The apparatus is easily used and can be packaged in a sealed and sterilized single-use package thereby reducing the possibility for cross-contamination and infection. More specifically, the instant invention in one embodiment is an apparatus for securing a tracheal tube, adjunct tube, an oropharyngeal tube, a nasogastric tube, a laryngeal tube or a laryngeal mask airway to a patient, comprising: (a) an elongate strip of adhesive tape having an adhesive side and a non-adhesive side; (b) a first peel-away tab on and covering the adhesive side of more than half the length of the adhesive tape; and (c) a second peel-away tab on and covering the adhesive side of the remaining portion of the adhesive tape.

In another embodiment, the instant invention is an improved kit of components for securing a tracheal tube, an adjunct tube, an oropharyngeal tube, a nasogastric tube, a laryngeal tube or a laryngeal mask airway to a patient, the kit of components contained in a sealed and sterilizable pouch, wherein the improvement comprises an improved adhesive tape, comprising: (a) an elongate strip of adhesive tape having an adhesive side and a non-adhesive side; (b) a first peel-away tab on and covering the adhesive side of more than half the length of the adhesive tape; and (c) a second peel-away tab on and covering the adhesive side of the remaining portion of the adhesive tape.

In yet another embodiment, the instant invention is an improved method for securing a tracheal tube, an adjunct tube, an oropharyngeal tube, a nasogastric tube a laryngeal tube or a laryngeal mask airway to a patient using an elongate strip of adhesive tape, comprising the steps of (a) peeling a first peel-away tab on and covering the adhesive side of more than half the length of an elongate strip of adhesive tape having an adhesive side and a non-adhesive side, the adhesive tape additionally having a second peel-away tab on and covering the adhesive side of the remaining portion of the adhesive tape; (b) wrapping the adhesive side of the central portion of the thus exposed adhesive side of the adhesive tape around the tube or airway, (c) applying the remaining portion of the adhesive side of the adhesive tape of step (a) to the cheek or upper lip of the patient; (d) peeling the second peel-away tab from the adhesive tape and applying the thus exposed adhesive side of the adhesive tape to the other cheek or upper lip of the patient thereby securing the tube or airway to the patient.

BRIEF DESCRIPTION OF THE DRAWINGS

FIG. 3 is a rear view in full of a portion of the apparatus shown in FIG. 1 after the longer peel-away tab has been removed and the central portion of the apparatus is wrapped around a tracheal tube or the like;

DETAILED DESCRIPTION

Figure 1:
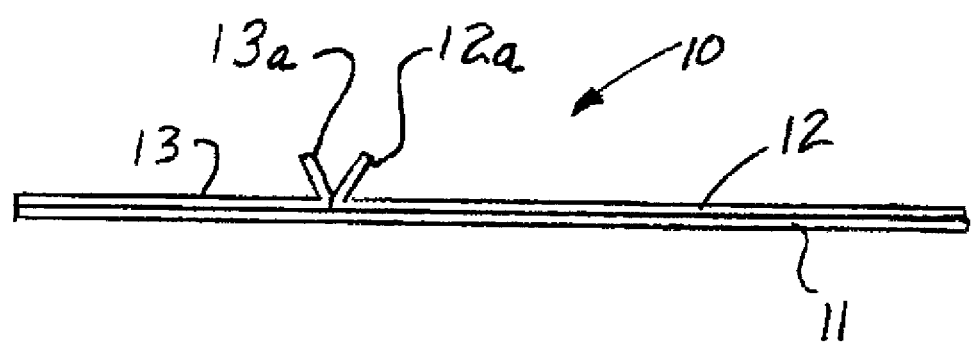
FIG. 1 is a side view in full of an apparatus embodiment of the instant invention showing two peel-away tabs on and covering the adhesive side of an elongate strip of adhesive tape.
Figure 2:
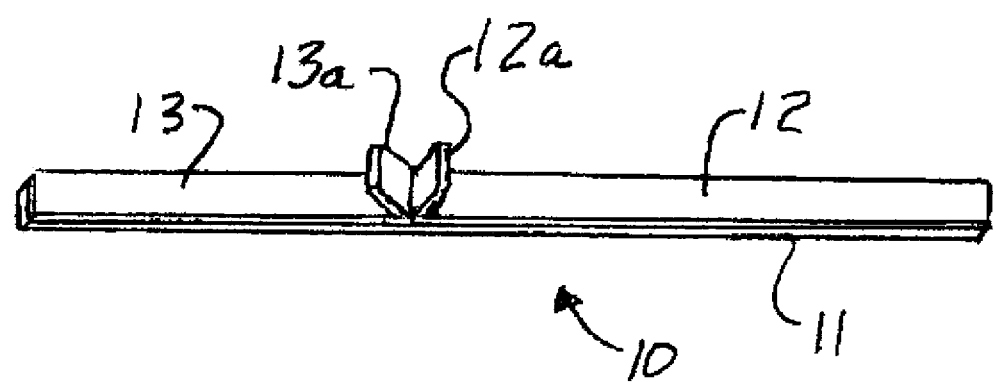
FIG. 2 is a perspective view in full of the apparatus shown in FIG. 1.

Referring now to FIG. 1, therein is shown a side view in full of an apparatus embodiment 10 of the instant invention. The apparatus 10 comprises an elongate strip of adhesive tape 11 having an adhesive side and a non-adhesive side. A second peel-away tab 13 is positioned on and covering less than half the length of the adhesive side of the adhesive tape 11. A first peel-away tab 12 is positioned on and covering more than half the length of the adhesive side of the adhesive tape 11. The pair of peel-away tabs 12 and 13 preferably have tab ends 12a and 13a so that the tabs 12 and 14 can be more easily peeled off the tape 11. Referring now to FIG. 2, therein is shown a perspective view of the apparatus 10 of FIG. 1.

Figure 3:
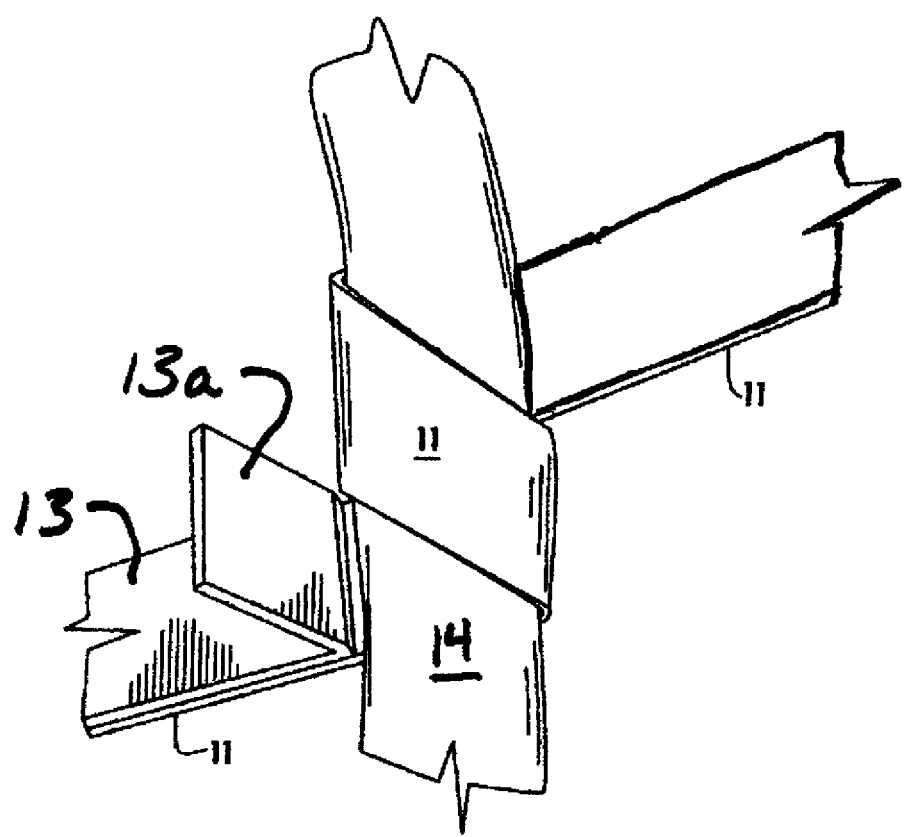
Figure 4:
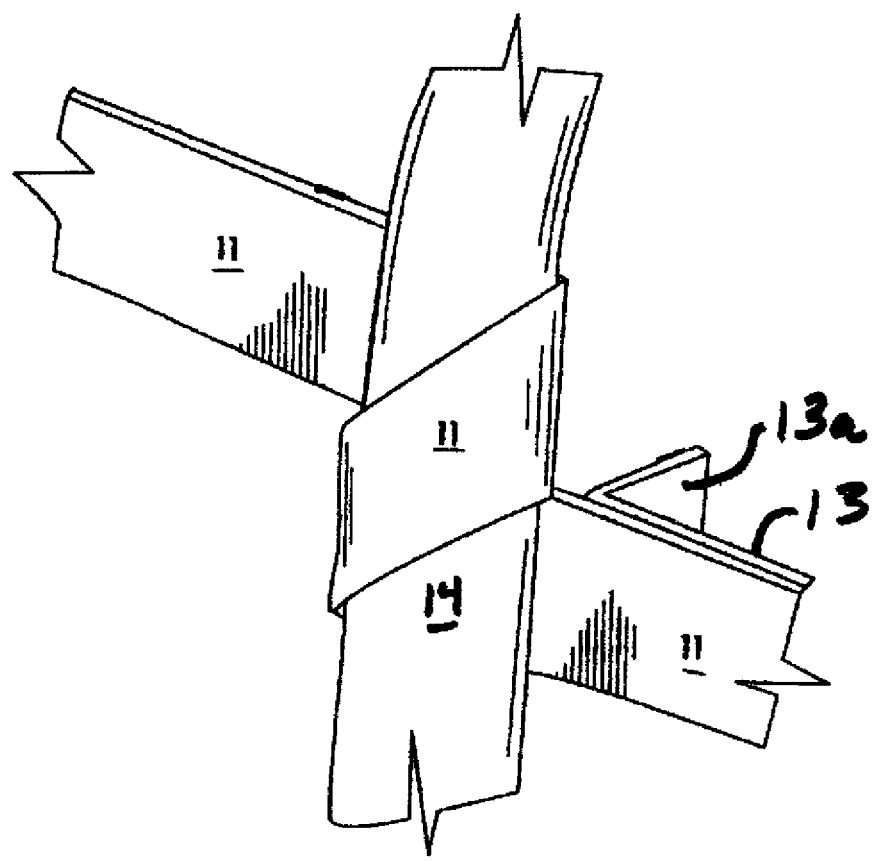
FIG. 4 is a front view in full of the system shown in FIG. 3 in position to pull the remaining peel-away tab from the tape.
Figure 5:
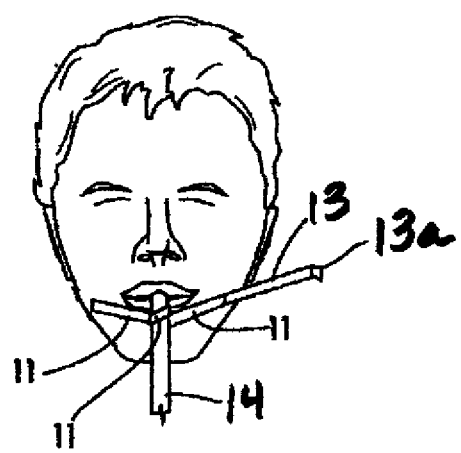
FIG. 5 is a front view in full of the system shown in FIG. 4 as the remaining peel-away tab is pulled from the tape end to adhere the tape end to the patient's cheek or upper lip.

Referring now to FIG. 3, therein is shown a rear view in full of a portion of the apparatus 10 shown in FIGS. 1 and 2 after the first peel-away tab has been removed and the central portion of the tape 11 has been wrapped around a tracheal tube 14. Referring now to FIG. 4, therein is shown a front view in full of the system shown in FIG. 3 in position to pull the remaining peel-away tab 13 from the tape 11. Referring now to FIG. 5, therein is shown front view in full of the system shown in FIG. 4 as the peel-away tab 13 is pulled from the tape 11 to adhere the remaining end of the tape 11 to the patient's cheek or upper lip thereby securing the tracheal tube to the patient.

Figure 6:
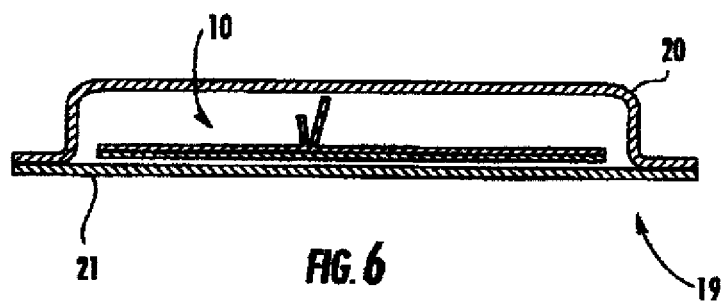
FIG. 6 is a side cross-sectional view of a kit of components for securing a tracheal tube, an adjunct tube, an oropharyngeal tube, a nasogastric tube, a laryngeal tube or a laryngeal mask airway to a patient, the kit of components contained in a sealed and sterilizable pouch and including the apparatus of FIG. 1.
Figure 7:
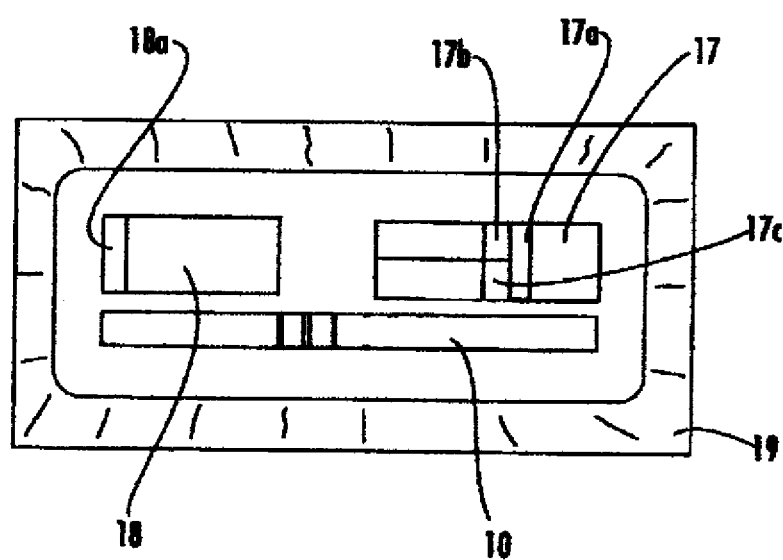
FIG. 7 is an upper view in full of the kit of components of FIG. 6 showing additional tape apparatus useful when securing a tracheal tube, an adjunct tube, an oropharyngeal tube, a nasogastric tube, a laryngeal tube or a laryngeal mask airway to a patient.

Referring now to FIG. 6, therein is shown a side cross-sectional view of a kit of components 19 for securing a tracheal tube to a patient, the kit of components contained in a conventional sealed and sterilizable pouch comprised on an upper formed transparent plastic film portion 20 sealed at the edges thereof to a lower paper portion 21, the kit 19 including the apparatus 10 of FIG. 1. Referring now to FIG. 7, therein is shown an upper view in full of the kit of components 19 of FIG. 6 showing additional tape apparatus 17 and 18 useful for securing nasogastric tubes to a patient and as eye tapes. Apparatus 17 is comprised of a piece of adhesive tape having an adhesive and non-adhesive sides and a bifurcated end. Peel-away tabs 17a, 17b and 17c are positioned on and covering the adhesive side of the adhesive tape. Apparatus 18 is simply comprised of a piece of adhesive tape having adhesive and non-adhesive sides. Peel-away tab 18a is positioned on and covering the adhesive side of the adhesive tape. The kit of components 19 can be sterilized and stored for use.

The adhesive tape used in the instant invention is preferably of the type suited for attachment to the skin, which can be sterilized by conventional means (such as exposure to ethylene oxide) and which will release the peel-away tabs without undue force. Such adhesive tape is well-known in the art. The peel-away tabs are preferably made of plastic coated paper and are also well-known in the art.

What is claimed is:

1. An improved method for securing a tracheal tube, an adjunct tube, and oropharyngeal tube, a nasogastric tube, a laryngeal tube or laryngeal mask airway to a patient using an elongate strip of adhesive tape, comprising the steps of: (a) peeling a first peel-away tab on and covering an adhesive side of more than half the length of an elongate strip of adhesive tape having the adhesive side and a non-adhesive side, the adhesive tape additionally having a second peel-away tab on and covering the adhesive side of a remaining portion of the adhesive tape; (b) wrapping the adhesive side of the central portion of the thus exposed adhesive side of the adhesive tape around the tube or airway, (c) applying the remaining portion of the adhesive side of the adhesive tape of step (a) to the cheek or upper lip of the patient; (d) peeling the second peel-away tab from the adhesive tape and applying the thus exposed adhesive side of the adhesive tape to the other cheek or upper lip of the patient thereby securing the tube or airway to the patient.

2. The method of claim 1 wherein the elongate strip of adhesive tape has (a) the adhesive side and the non-adhesive side: (b) the first peel-away tab on and covering the adhesive side of more than half the length of the adhesive tape; and (c) the second peel-away tab on and covering the adhesive side of the remaining portion of the adhesive tape, wherein the first peel-away tab and the second peel-away tab each include an end tab which facilitate removal of the peel-away tabs from the adhesive side of the tape, wherein the end tab of the second peel-away tab is covered by the first peel-away tab, and wherein the apparatus is adapted to being wrapped around so as to encircle the adjunct tube, the oropharyngeal tube, the nasogastric tube, or the laryngeal tube and for securing the adjunct tube, the oropharyngeal tube, the nasogastric tube, or the laryngeal tube to the cheek or upper lip of the patient.

3. The method of claim 2 wherein before peeling, the end tab of the first peel-away tab faces the end tab of the second peel-away tab.

4. The method of claim 3 wherein the first peel-away tab has an essentially flat outer surface.

5. The method of claim 4 wherein the flat outer surface of the first peel-away tab is in the form of a rectangle.

6. The method of claim 5 wherein the end tab of the second peel-away tab facilitates removal of the peel-away tab from the adhesive side of the adhesive tape.

7. The method of claim 6 wherein the end tab of the second peel-away tab extends away from the adhesive side of the adhesive tape.

8. The method of claim 7 wherein the end tab of the second peel-away tab extends toward an end of the adhesive tape which is covered by the second peel-away tab.

* * * * *